United States Patent [19]

Lyon

[11] Patent Number: 4,536,844

[45] Date of Patent: Aug. 20, 1985

[54] METHOD AND APPARATUS FOR SIMULATING AURAL RESPONSE INFORMATION

[75] Inventor: Richard F. Lyon, Palo Alto, Calif.

[73] Assignee: Fairchild Camera and Instrument Corporation, Mountain View, Calif.

[21] Appl. No.: 488,886

[22] Filed: Apr. 26, 1983

[51] Int. Cl.³ .......... A61N 1/36

[52] U.S. Cl. .......... 364/487; 128/419 R; 179/107 FD

[58] Field of Search .......... 128/746, 784-786, 128/789, 419 R, 421; 181/129-135; 381/68; 179/107 R, 107 PC, 107 BC, 107 E, 107 FD; 328/105; 364/578, 487

[56] References Cited

U.S. PATENT DOCUMENTS 4,428,377 1/1984 Zollner et al. .......... 128/419 R

FOREIGN PATENT DOCUMENTS 2811120 9/1978 Fed. Rep. of Germany ... 128/419 R

WO83/00999 3/1983 PCT Int'l. Appl. .......... 128/784

OTHER PUBLICATIONS

Merzenich et al., "Cochlear Implant Prosthesis: Strategies and Progress", *Annals of Biomed. Engr.*, vol. 8, 1980, pp. 361-368.

White, "Review of Current Status of Cochlear Prostheses", *IEEE Trans. on Biomed. Engr.*, vol. BME-29, No. 4, 4-1982, pp. 233-238.

Dillier et al., "Computer-Controlled Test System for Electrical Stim. of the Auditory Nerve of Deaf Patients w/Impl. Microelect.", *Scand. Audiol. Suppl. II*, 1980, pp. 163-170.

Forster, "Theor. Des. and Implementation of a Transcut, Multichannel Stimulator For Nevr. Prosthesis Applic.", J. Biomed. Engng, vol. 3, No. 2, 4-1981, pp. 107-120.

Allen, J. B., "Cochlear Modeling-1980", ICASSP 81, pp. 766-789, Atlanta, 1981.

Nilsson, H. G., "A Comparison of Models for Sharpening of Frequency Selectivity in the Cochlea", Biological Cypernetics 28, pp. 177-181, 1978.

Schroeder et al., "Model for Mechanical to Neural Transduction of the Auditory Receptor", JASA 55, pp. 1055-1060, 1974.

Kim et al., "A Population Study of Cochlear Nerve Fibers: Comparison of Spatial Distributions of Average-Rate and Phase Locking Measures of Responses to Single Tones", Journal of Neuro-Physiology 42, pp. 16-30, 1979.

Zwislocki, J. J., "Sound Analysis in the Ear: A History of Discoveries", American Scientist, 69, pp. 184-192, 1981.

Zweig et al., "The Cochlear Compromise", JASA 59, pp. 975-982, 1976.

Schroeder, M. R., "An Integrable Model for the Basilar Membrane", JASA 53, pp. 429-434, 1973.

Zweig, "Basilar Membrane Motion", Cold Spring Harbor Symposia on Quantitative Biology, vol. XL, pp. 619-633 (Cold Spring Harbor Laboratory, 1976).

*Primary Examiner*—Lee S. Cohen

*Assistant Examiner*—Angela D. Sykes

*Attorney, Agent, or Firm*—Townsend and Townsend

[57] ABSTRACT

Speech and like signals are analyzed based on a model of the function of the human hearing system. The model of the inner ear is expressed as signal processing operations which map acoustic signals into neural representations. Specifically, a high order transfer function is modeled as a cascade/parallel filterbank network of simple linear, time-invariant second-order filter sections. Signal transduction and compression are based on a half-wave rectification with a non-linearly coupled, variable time constant automatic gain control network. The result is a simple device which simulates the complex signal transfer function associated with the human ear. The invention lends itself to implementation in digital circuitry for real-time or near real-time processing of speech and other sounds.

19 Claims, 8 Drawing Figures

METHOD AND APPARATUS FOR SIMULATING AURAL RESPONSE INFORMATION

BACKGROUND OF THE INVENTION

1. Field of Invention

This invention relates to signal processing generally, and more particularly, to the analysis of sound based on models of human audition. Specifically, the invention relates to a method and apparatus for use in high quality speech detection and recognition.

It has been pointed out that to understand the hearing process is to understand the cochlea. Moreover, it is generally recognized that sounds are best characterized in a frequency domain and that the cochlea performs the job of transforming the incoming time-domain pressure signal into this other domain. The exact nature of this frequency domain has not been well clarified and, in fact, has led to some misunderstandings as to the nature of the so-called frequency domain associated with aural perception. Ohm's acoustic law is particularly misleading in that it asserts that the ear is insensitive to phase. Concepts such as smoothed filterbank envelopes, linear predictive coding spectra and the like have never been able to successfully distinguish between complex single sounds and separate unfusible sounds with similar short-term spectra. As a consequence, speech and other sounds have been extremely difficult to reliably decode, and the widespread need for reliable sound and speech recognition systems has gone unfilled.

2. Description of the Prior Art

Typical prior art speech recognition methods and apparatus have been modeled on the assumption that the ear is relatively insensitive to phase, or small values of group delay. Current speech analysis techniques fail to effectively deal with sounds other than pure, simple speech sounds.

Many cochlea models have been suggested in the past. Most are models of only mechanical motion of the basilar membrane to various degrees of fidelity. Some hearing models include a "second filter" of various sorts, transduction nonlinearities and simple compression mechanisms. See, for example, Allen, J. B., "Cochlear Modeling-1980" ICASSP 81, pp. 766–789, Atlanta, 1981; Nilsson, H. G. "A Comparison of Models for Sharpening of Frequency Selectivity in the Cochlea," Biological Cybernetics 28, pp. 177–181, 1978; Schroeder et al., "Model for Mechanical to Neural Transduction of the Auditory Receptor," JASA 55, pp. 1055–1060, 1974; and Kim et al., "A Population Study of Cochlear Nerve Fibers: Comparison of Spatial Distributions of Average-Rate and Phase-Locking Measures of Responses to Single Tones," Journal of Neurophysiology 42, pp. 16–30, 1979.

Much work has been done in the mechanical modeling of the cochlea, although little has been applied to the speech analysis field. See, for example, Zwislocki, J. J., "Sound Analysis in the Ear: A History of Discoveries," American Scientist, 69, pp. 184–192, 1981; Matthews, J. W., "Mehcanical Modeling of Non-Linear Phenomena Observed in the Peripheral Auditory System," Doctor of Science Thesis, Washington University, St. Louis, Mo. 1980; Neely, S. T., "Fourth-Order Partition Dynamics for a Two-Dimensional Model of the Cochlea," Doctor of Science Thesis, Washington University, St. Louis, Mo. 1981; Zweig et al., "The Cochlear Compromise" JASA 59, pp. 975–982, 1976; Schroeder, M. R., "An Integrable Model for the Basilar Membrane," JASA 53, pp. 429–434, 1973; and Zweig, "Basilar Membrane Motion," Cold Spring Harbor Symposia on Quantitative Biology, Volume XL, pp. 619–633 (Cold Spring Harbor Laboratory, 1976).

SUMMARY OF THE INVENTION

According to the invention, a method and apparatus for detecting, analyzing and recognizing speech and other sounds comprises a model which mimics the behavior of the cochlea to preserve those aspects of sound most relevant to sound separation and speech parameterization. In particular, the interacting behaviors of the basilar membrane and parts of the cochlea, such as the organ of Corti, are separated into non-interacting models. The technique is implemented by simple time-invariant filtering, followed by half-wave detection and, finally, a complex nonlinear compression of the dynamic range of the mechanical domain into a much smaller range appropriate for an internal representation similar to the human neural representation.

In a specific embodiment, the cochlear model is based on computationally attractive second-order digital filter sections implemented by multipliers and delays. Only conventional time-domain signal flow-graph kinds of computations are required so that the technique is suitable for implementation in either general-purpose or special-purpose computing architecture. The technique can be implemented in a machine capable of operating in real time where speech is sampled at a rate of twenty kHz with a few million multiplications per second. Sixty or more parallel channels may be used to generate spectrogram type images of speech sounds which can be employed in speech recognition and ultimately symbolic understanding techniques.

It has been discovered that the gain of an automatic gain control circuit or dynamic range compressor is generally subject to time constants which are strongly dependent on the input signal level. These time constants can have a substantially adverse effect on the output signal integrity, causing useful information to be either clipped or to be lost due to insufficient signal level. According to the invention, the effect of time constant-induced distortion can be minimized by using a controlled-gain element with a super-linear control function whereby the effective time constant variation is minimized. As a further simplification, the super-linear control function can be approximated by the use of a cascade of stages of bilinear elements with separate control signals, time constant and degree of coupling from adjacent channels.

The invention will be best understood by reference to the following detailed description taken in connection with the accompanying drawings.

DESCRIPTION OF SPECIFIC EMBODIMENTS

According to the invention, the model of the inner ear is a network of linear time-invariant bandpass filters arranged in a cascade/parallel filterbank whose input is a signal representative of a sound and whose output is a half-wave rectified signal employing a nonlinear coupled automatic gain control for signal compression. Apparatus according to the invention may be implemented either in analog circuitry or in digital circuitry. Analog circuit implementation will be apparent to those of ordinary skill in the art from the description herein. Moreover, advances in very large scale digital circuit design permit reasonably straight-forward adaption of computational models to either special-purpose computing architecture or general-purpose computing architecture which implement conventional time-domain signal flow computations. The disclosure hereinafter will employ both time-domain and frequency-domain descriptions of signal processing, as appropriate, for explaining the characteristics of the subject invention.

Figure 1:
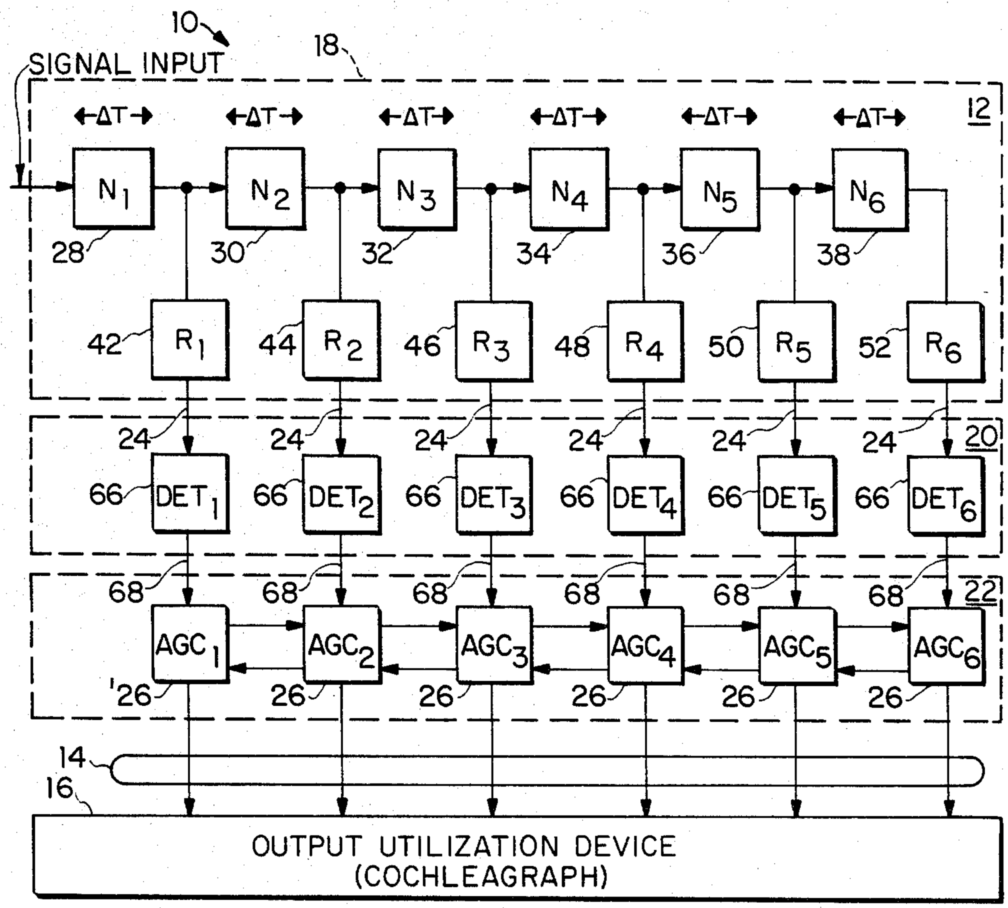
FIG. 1 is a block diagram of a filterbank representative of a cochlea model according to the invention.

Referring to FIG. 1, there is shown a block diagram representation of a simulated ear 10 according to the invention. The simulated ear is a computational model of the cochlea suitable for physical implementation in either analog circuitry or in digital circuitry suitable for real-time simulation of cochlear response characteristic. More specifically, the simulated ear 10 receives an analog input signal or its equivalent at a signal input 12, which signal represents the full spectrum of sounds to be analyzed, and delivers a set of synchronous outputs through an output bus 14 which simulates real-time neural response to sounds within predefined frequency channels. In a preferred embodiment, the output bus 14 provides sixty-four (64) distinct frequency channels of response to an output utilization device such as a cochleagraph 16. The cochleagraph 16 is operative to map the time-dependent amplitude response of the simulated ear 10 as a function of frequency. The neural representation of sounds is as patterns and spikes in a time-frequency plane.

The simulated ear 10 comprises three elements, namely, a cochlear filterbank 18, a detector bank 20 and an adaptive compressor bank 22. The cochlear filterbank 18 receives an input signal via signal input 12, which, in turn, supplies signals distributed over frequency passbands through spectral channel paths 24 to the detector bank 20. The detector bank 20, as hereinafter explained, rectifies and filters channelized signals, which, in turn, are conveyed to the adaptive compressor bank 22. As hereinafter explained, each channel of the adaptive compressor bank 22 provides a variable gain across time and frequency dimensions, maintains sharp peaks and clean valleys in the amplitude of the signal, and de-emphasizes gradual loudness changes. Portions of the output signal of each automatic gain control element 26 are conveyed to neighboring AGC elements 26, thereby to simulate the physiological phenomenon of lateral inhibition. Lateral inhibition is a phenomenon whereby sensory neurons receiving a high stimulation reduce their response as well as the response of nearby neurons by way of lateral distribution of their outputs to neighboring sensory neurons.

Referring to FIG. 1, the cochlear filterbank 18 is constructed to preserve both the frequency and time-domain functions performed by the cochlea when transforming incoming time-domain pressure signals into neural signals. To this end, the interacting behaviors of the basilar membrane in the organ of Corti have been separated into non-interactive models. The cochlear filterbank 18 reduces to a set of linear, time-invariant filters, and nonlinear effects are accounted for in the adaptive compressor bank 22.

Figure 2A:
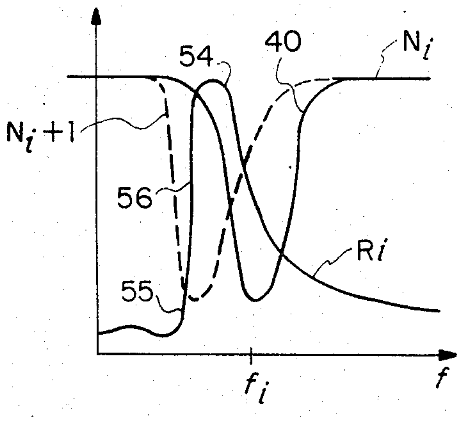
FIG. 2A and FIG. 2B together are plots of transfer functions of filters employed in the filterbank according to the invention.

The basilar membrane operation may be modeled by a conventional RLC transmission-line analog to a one-dimensional, long-wave hydrodynamic model. For a given frequency, a pressure wave propagates with an identifiable wavelength and attenuation without reflection. The model for one channel is readily reduced to practice and realized as a notch filter. Both pressure and velocity components of the membrane operation can be identified in the model. In a complex plane, a notch filter is formed by providing a high-Q zero pair near a lower-Q pole pair of a biquadratic transfer function. Biquadratic filters are cascaded as, for example, in FIG. 1, as filter 28, filter 30, filter 32, filter 34, filter 36 and filter 38. While only six filters are shown, it is understood that preferably about sixty-four (64) biquadratic cascaded filters may be provided in a preferred embodiment, where the center frequency of each notch filter changes approximately geometrically starting at about twenty (20) kHz adjacent the input end, and terminating at about fifty (50) Hz. That is, the first notch filter 28 has a notch at about twenty (20) kHz and the last notch filter 38 has a notch at about fifty (50) Hz. The ratio of channel to channel frequency is selected to be approximately constant and less than unity, whereby a logarithmic frequency and time characteristic is approximated at higher frequencies and which is approximately linear at lower frequencies. The outputs of each of the notch filters 28, 30, 32, 34, 36 and 38 are analogous to a pressure signal. Curve 40 in FIG. 2A illustrates a typical characteristic of a biquadratic filter transfer function of a notch filter $N_i$ whose notch is centered at a frequency $f_i$. Associated with each notch filter is an inherent finite delay corresponding to a minimum-phase transfer function and based on the spacing between the input and the termination within the cochlea. The notch filter cascade constructed of notch filters $N_i$ form a collection of minimum-phase lowpass filters with very steep rolloffs.

Figure 2B:
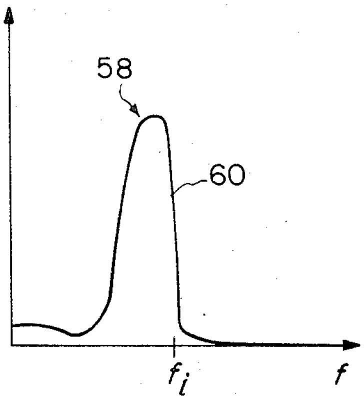

The velocity of motion of the basilar membrane is modeled by providing a bank of bandpass filters or resonators each designated $R_i$, represented herein as resonator 42, resonator 44, resonator 46, resonator 48, resonator 50 and resonator 52. Each resonator $R_i$ is coupled to shunt a signal representing membrane velocity in the path between notch filters to spectral channel paths 24. Referring to FIGS. 2A and 2B, each resonator may be realized as a second-order filter with a zero in the complex plane at DC and a high-Q pole pair located between the previous notch filter zero pair and the next notch filter zero pair. Curve 54 in FIG. 2A illustrates the transfer function for a resonator $R_i$. The resonant frequency of the resonator $R_i$ is at a lower frequency than the minimum frequency of the previous notch filter $N_i$ in series therewith as represented by Curve 40, and higher than the center frequency of the next notch filter $N_{i+1}$ in the cascade, as represented by Curve 56. The resonator $R_i$ may optionally be provided with higher order zero pairs at the lower frequencies, as indicated by the dip 55, for resonance control. Referring to FIG. 2B, there is shown the composite transfer function 58 at a center frequency $f_i$ at the output of any one of the resonators $R_i$. This composite transfer function is characterized by a very sharp high frequency rolloff 60 which is a minimum-phase repesentation of the signal.

Each signal on line 24 represents velocity. Together, the bank of notch filters $N_i$ and resonators $R_i$ define a cascade of second-order notches and a parallel collection of second-order bandpass filters which present at an output a composite transfer function which is an asymmetric bandpass function which simultaneously provides good frequency resolution. Furthermore, it has the useful property that the sum of the orders of the transfer functions from the input 12 to the plurality of outputs 24 greatly exceeds the total of the orders of the component sections. In other words, it achieves an economy of components by utilization of the same filter sections in a plurality of high-order transfer functions which together directly model the structure of a segmented cochlear transmission line. All of the filters and transfer functions herein described can be equally well implemented with either continuous-time or discrete-time techniques, in either analog or digital technologies. Moreover, the general cascade/parallel filterbank structure may be modified as appropriate for better cochlear modeling to improve resolution in the region of maximum speech information, or to reduce cost. Modifications may take the form of, for example, changing the frequency spacing or varying the Q, particularly near the extremes of the frequency band of interest. The cascade/parallel filterbank defining the cochlear filterbank 18 is operative to separate complex mixtures of sound into high-signal-to-noise-ratio regions, principally by separating different frequencies into different channels which inherently preserve enough time resolution to separate response to individual pitch pulses. As a consequence, simultaneous voiced speech sounds which differ in some speech formants and in pitch can be separated into recognizably distinct patterns of activity when the output signals are analyzed.

The output 24 to the detector bank 20 must be converted to a more useful form for subsequent signal processing. It is intended that the high frequency components of the signal be represented consistent with representation of the low frequency components. The neural representation of signals has a bandwidth at least as great as the full range of voice pitch. This permits the representation of the time structure of formant-frequency carriers as amplitude modulated at a pitch rate with a range of low-frequency "carriers" which can be synchronously represented in the output bandwidth. Conversion to a more useful form implies processing by a detection non-linearity, such as rectification, or envelope detection. Because there is considerable physiological evidence that there is a half-wave detection function in the hair cells of the organ of Corti, simple half-wave rectification has been selected as the basis of detection.

Figure 3A:
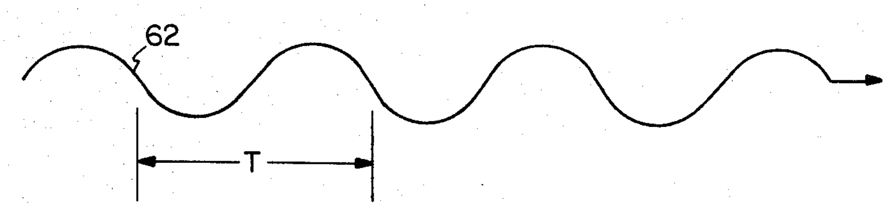
FIGS. 3A, 3B, 3C and 3D are waveform diagrams illustrating a rectification technique according to the invention.
Figure 3B:
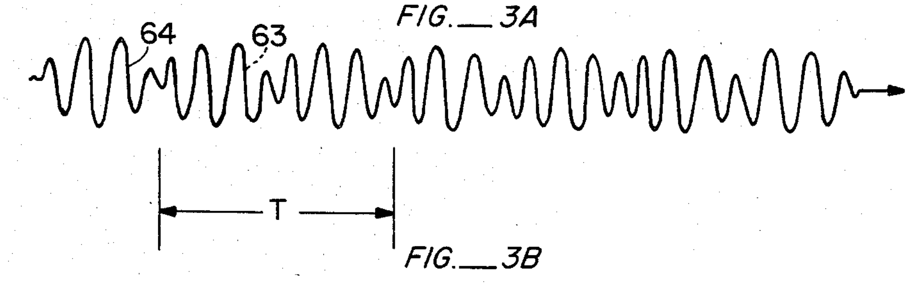
Figure 3C:
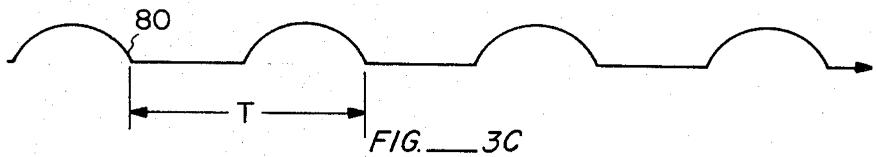
Figure 3D:
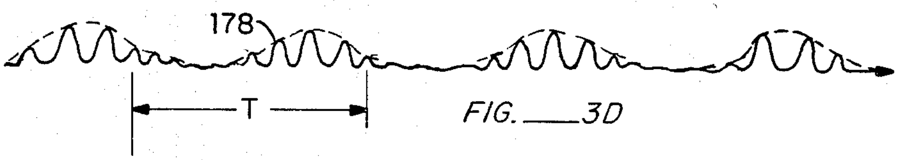

Referring to FIGS. 3A, 3B, 3C and 3D and, particularly, first to FIG. 3A, each sound signal may be considered to be a formant frequency carrier 62 having a pitch period T (FIG. 3A) which is amplitude modulated to form a modulated signal 64 having an envelope 63 at the fundamental pitch (FIG. 3B). It is important to be able to reproduce a detected signal which is perceived as having the same pitch. Half-wave rectification preserves the pitch period, as shown in FIG. 3C. According to the invention, each output signal on output signal lines 24 is applied through a broad band detector 66 (FIG. 1) which is operative as a half-wave rectifier and wide bandwidth lowpass filter. FIG. 3D illustrates a half-wave rectified signal 178 having the same perceived pitch period as the input signal. FIG. 3C illustrates a rectified signal at the fundamental pitch which has the same period T as the input signal. Lowpass filtering is employed to obtain a bandwidth consistent with the bandwidth of the neural domain which is being modeled. The neural representation of signals has a bandwidth of at least as high as the full range of voice pitch, and it generally exceeds about two (2) kHz which is a much broader bandwidth than detection techniques employed heretofore. This bandwidth is generally enough to preserve all relevant information within signal 78 (FIG. 3D). A half-wave detection signal envelope illustrated by waveform 80 (FIG. 3C) represents a comparable half-wave rectifier.

Figure 4:
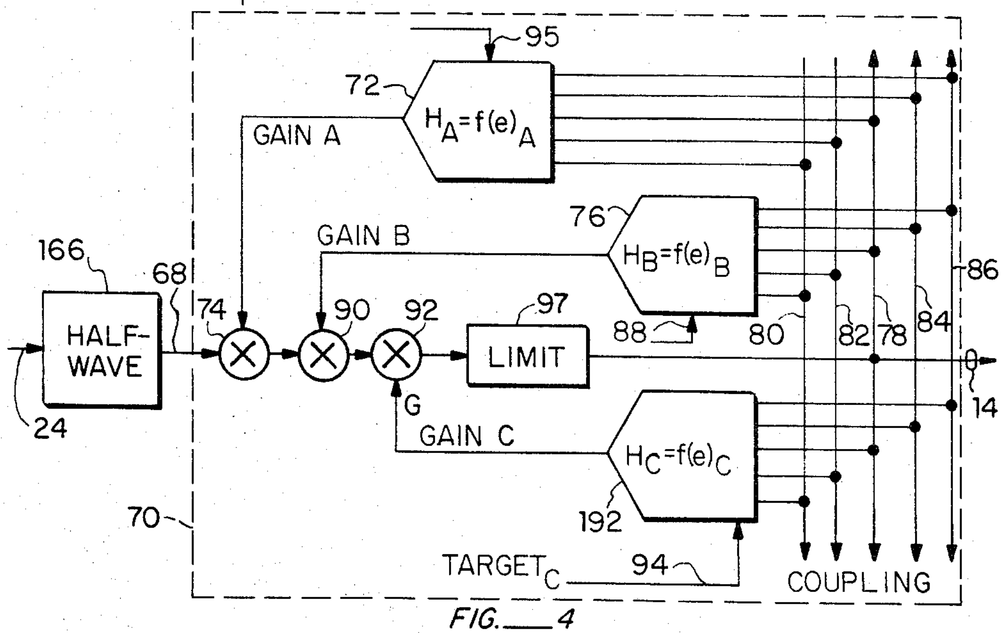
FIG. 4 is a block diagram of one channel of a detector and compressor according to the invention with coupled-automatic gain control.

The output signals of the detectors 66 are each applied via line 68 to automatic gain control elements 70 of the adaptive compressor bank 22 (FIG. 1 and FIG. 4). FIG. 4 is illustrative of one automatic gain control element 70 and will be explained hereinafter.

Heretofore no automatic gain control circuit has been able to handle the kinds of signal ranges and achieve the degree of signal compression achievable by the human ear without severely distorting signal quality. Typically, there is an effective flattening of amplitude peaks, and there is severely unstable or noisy behavior in the presence of low signals. To achieve a useable adaptation mechanism in an adaptive compressor bank 22 according to the invention, there must be a varying gain characteristic across time and frequency dimensions, sharp peaks of amplitude, clean low-noise signals, emphasis on attack and termination of sound in the form of increase in amplitude, de-emphasis of overall spectral tilt and gradual loudness changes. To this end, a neural transduction model has been formulated similar to physiological models. (See, for example, Schroeder et al., "Model for Mechanical to Neural Transduction in the Auditory Receptor," JASA 55, pp. 1055–1060, 1974.) The adaptive compressor bank 22 according to the invention comprises a plurality of single channel automatic gain control elements whose gain characteristics are developed from the signal source and from gains developed from several other automatic gain control elements 26 adjacent in time and/or frequency. The gain factor thereof can be employed as a gain control signal which adjusts overall signal level independent of frequency and time. In the embodiment of FIG. 4, a first gain control element 72 is operative to control a simple multiplier 74 at the element 26 input through line 68. The first gain control element 72 is responsive to a plurality of input signals on lines 78, 80, 82, 84 and 86.

The second gain element stage comprises a second gain control element 76 which is responsive to a plurality of input signals including an output feedback signal on channel feedback line 78, a plurality of output feedback signals on adjacent channel feedback lines 80, 82, 84 and 86 and a reference signal on a first target signal line 88. The output of the second gain control element 76 is provided to a second cascaded multiplier 90. A third gain control element 192 receives as input controls feedback signals through channel feedback signal line 78 and adjacent channel feedback signal lines 80, 82, 84 and 86 as well as a second reference signal via second target signal line 94. A third target signal line 95 controls the first gain control element 72. The output of second gain control element 76 is applied to a third multiplier 92 in the cascade. The output of the third multiplier 92 is provided to a limiter 97, the function of which is to assure a bounded output signal in response to an unbounded input signal. The output of the limiter 97 is provided to channel feedback signal line 78 and as a channelized signal on bus 14. The automatic gain control element 26 may be implemented in either analog circuitry or in discrete-time digital circuitry.

An implementation of a discrete-time coupled-AGC compression network as shown in FIG. 4 is operative according to the following equations. For each channel of the adaptive compressor bank 22:

$$\text{Output}_i = \text{Limit}[\text{Detect}_i\,\text{Gain}_A\,\text{Gain}_{B,i}\,\text{Gain}_{C,i}] \quad 1.$$

$$\text{Gain}_{C,i} = Z^{-1}[(1 - e_C)\text{Gain}_{C,i} - e_C(\text{Wt}_{C,i}\cdot(\text{Output}_i - \text{Target}_{C,i}))] \quad 2.$$

$$\text{Gain}_{B,i} = Z^{-1}[(1 - e_B)\text{Gain}_{B,i} - e_B(\text{Wt}_{B,i}\cdot(\text{Output}_i - \text{Target}_{B,i}))] \quad 3.$$

$$\text{Gain}_A = Z^{-1}[(1 - e_A)\text{Gain}_A - e_A(\text{Wt}_A\cdot(\text{Output}_i - \text{Target}_{A,i}))] \quad 4.$$

where each Output is the value of the signal which represents an element of the spectrogram provided to the output utilization device 16 on each line of the signal bus 14;

each Detect is the output of each of the detectors 66;

each Target is approximately the desired output signal level with different Targets (A,B,C) for each loop;

each $\text{Gain}_A$ is the gain control signal which adjusts overall signal level independent of channel;

each $\text{Gain}_B$ and $\text{Gain}_C$ are, respectively, levels of per-channel gains;

$\text{Wt}_A$ is the weighting from all channels relative to the overall gain;

$\text{Wt}_B$ and $\text{Wt}_C$ are the cross-coupling weightings from some or all of the channels to the subject channel;

$e_A$, $e_B$, $e_C$ are a small gain or leak-rate which determines the loop time constant;

i is the index which varies from 1 to the number of channels in use; and the dot (·) is the vector inner dot product function; and $Z^{-1}$ is the unit time delay operator which is used only in discrete time system. In analog systems, this operation is unnecessary.

The slowest time constant is the sampling interval divided by $e_A$ ($T/e_A$ for sampling interval T). Faster filter time constants are $T/e_B$ and $T/e_C$.

The loops with longer time constants and thus smaller values of e are the outer loops (A,B) and should have smaller target values than the inner loops (C and possibly D, E, etc.).

Preferably the compressive nonlinearity of the limiter 94 is somewhat higher than the target value for $\text{Target}_C$, the desired short-term average output. In the preferred embodiment, this design should provide a sixty (60) dB or greater accommodation in input signal level.

An apparatus according to the invention implemented with discrete-time digital signal processing techniques can be made operative in real-time with reasonable accuracy if all second-order sections are implemented with five (5) multiplications per sample, the sample of a speech signal is at 20 kHz (that is giving it 200,000 multiplications per second per channel). Sixty-four (64) channels in time and frequency result in 12.8 million multiplications per second. State of the art VLSI technology is capable of providing adequate signal storage and signal processing within these limitations with a relatively small number of silicon integrated circuits.

The invention now has been explained with reference to specific embodiments. Other embodiments will be apparent to those of ordinary skill in the art. It is, therefore, not intended that this invention be limited except as indicated by the appended claims.

What is claimed is:

1. A method for simulating neural response of an ear comprising:

filtering an input signal representative of sound stimuli through a first filtering means, said first filtering means producing first response characteristics to said stimuli, said first response characteristics being divided into a plurality of channels as channelized frequency band limited signals; thereafter half-wave detecting each one of said channelized frequency band limited signals representative of said first response characteristics over a relatively broad band to produce a plurality of frequency channelized detected signals;

compressing said frequency channelized detected signals in each said channel as a function of amplitude of frequency channelized detected signals in other channels to produce output electronic signals; and providing said electronic output signals to an output utilization means.

2. The method of claim 1 wherein said filtering step comprises linearly and time-invariantly filtering said input signal into a minimum-phase representation of said frequency band-limited signals.

3. The method of claim 1 wherein said filtering step further comprises distributing said input signal over time to provide a plurality of channelized signals each having a different delay associated therewith, wherein the ratio of channel to channel frequency is selected to be approximately constant and less than unity.

4. The method according to claim 1 wherein said filtering step comprises combining a plurality of notch filters arranged in cascade with a plurality of resonant bandpass filters arranged in parallel, each said bandpass filter being coupled to receive said input signal through a different number of said notch filters.

5. A method for simulating neural response of an ear comprising:

separating an input signal into a plurality of channels of frequency band-limited signals, each band-limited signal having a different time delay relative to said input signal associated therewith, said separating comprising combining a plurality of notch filters arranged in cascade with a plurality of resonant bandpass filters arranged in parallel, each said bandpass filter being coupled to receive said input signal through a different number of notch filters;

detecting each one of said band-limited signals to produce a plurality of corresponding channelized output signals; and providing said channelized output signals to an output utilization means.

6. The method according to claim 5 wherein said separating step comprises establishing time delay for output of each one of said band-limited signals as a function which is in inverse proportion to frequency of said band-limited signals, wherein the ratio of channel to channel frequency is selected to be approximately constant and less than unity.

7. The method according to claim 5 further including compressing each one of said band-limited signals by compression of each one of said band-limited signals in direct proportion to compression of said channelized output signals in other channels.

8. The method according to claim 7 wherein compression factors are adjusted in accordance with at least two linearly variable-gain functions in cascade.

9. The method according to claim 7 further including the step of limiting upper frequency response of said band-limited signals to simulate response within a neural response bandwidth.

10. An apparatus for processing an input signal having information distributed in time and frequency comprising:

means responsive to said input signal for separating said input signal into a plurality of frequency band-limited signals, each band-limited signal having a different time-delay relative to said input signal associated therewith;

means for half-wave rectifying each one of said band-limited signals to produce rectified band-limited signals; and means for compression each one of said rectified band-limited signals in proportion to amplitude of corresponding rectified band-limited signals and in proportion to other ones of said rectified band-limited signals to produce a plurality of compressed, rectified band-limited channelized output signals distributed in time.

11. The apparatus according to claim 10 wherein said separating means in operative to delay output of each one of said band-limited signals within band-limited channels in inverse proportion to frequency of said corresponding one of said band-limited signals.

12. The apparatus according to claim 11 wherein said compressing means is operative to increase compression of each one of said rectified band-limited signals in direct proportion to compression of compressed, rectified band-limited channelized output signals in channels which are adjacent in channel frequency.

13. The apparatus of claim 12 wherein compressing factors of said compressing means are adjusted in accordance with at least two linearly time-invariant functions in cascade.

14. The apparatus according to claim 12 wherein variable time constants are associated with compression magnitude of each compressing means in proportion to amplitude of signal energy within pass-bands of adjacent frequency compressing means and in proportion to amplitude of signal energy within an associated pass-band.

15. The apparatus according to claim 12 wherein said compressing means is operative in accordance with the following relationships for each channel of said compressing means $$\text{Output}_i = \text{Limit}[\text{Detect}_i\ \text{Gain}_A\ \text{Gain}_{B,i}\ \text{Gain}_{C,i}] \quad 1.$$

$$\text{Gain}_{C,i} = Z^{-1}[(1 - e_C)\text{Gain}_{C,i} - \quad 2.$$

-continued $$e_C(\text{Wt}_{C,i} \cdot (\text{Output}_i - \text{Target}_{C,i}))]$$

$$\text{Gain}_{B,i} = Z^{-1}[(1 - e_B)\text{Gain}_{B,i} - e_B(\text{Wt}_{B,i} \cdot (\text{Output}_i - \text{Target}_{B,i}))] \quad 3.$$

$$\text{Gain}_A = Z^{-1}[(1 - e_A)\text{Gain}_A - e_A(\text{Wt}_A \cdot (\text{Output}_i - \text{Target}_{A,i}))] \quad 4.$$

where each Output is the value of the signal which represents an element of a spectrogram provided to an output utilization device on each line of a signal bus;

each Detect is the output of each of said rectifying means;

each Target is approximately the desired output signal level with different Targets (A,B,C) for each feedback loop;

each $\text{Gain}_A$ is the gain control signal which adjusts overall signal level independent of channel;

each $\text{Gain}_B$ and $\text{Gain}_C$ are, respectively, levels of per-channel gains;

$\text{Wt}_A$ is the weighting from all channels relative to overall gain;

$\text{Wt}_B$ and $\text{Wt}_C$ are cross-coupling weightings from at least some of the channels to the channel of Output;

$e_A$, $e_B$, $e_C$ are a small gain or leak-rate which determines loop time constant;

i is the index which varies from 1 to the number of channels in use;

the dot (·) is the vector inner dot product function; and $Z^{-1}$ is the unit time delay operator which is employed only in discrete time systems.

16. The apparatus according to claim 11 wherein said separating means is operative within channels between 20 kHz and 50 Hz.

17. The apparatus according to claim 11 wherein said separating means is a cascade of second-order notch filters, each notch filter having a different notch frequency, and a bank of second-order bandpass filters, each bandpass filter coupled to receive a signal through at least one of said second-order notch filters.

18. The apparatus according to claim 17 wherein each said notch filter and each said bandpass filter are paired in frequency to provide an asymmetric bandpass function with a relatively precise frequency passband and relatively precise time delay with respect to signal energy within said passband.

19. An apparatus for processing an input signal having information distributed in time and frequency comprising:

means responsive to said input signal for separating said input signal into a plurality of frequency band-limited signals, each band-limited signal having a different time delay relative to said input signal associated therewith, said separating means comprising a combination of a plurality of notch filters arranged in cascade with a plurality of resonant bandpass filters arranged in parallel, each said bandpass filter being coupled to receive said input signal through a different number of notch filters.

* * * * *